United States Patent [19]
Inagaki et al.

[11] Patent Number: 5,232,434
[45] Date of Patent: Aug. 3, 1993

[54] FLUID FEEDING PUMP UNIT

[75] Inventors: Yoshitaka Inagaki, Aichi; Rika Fujita; Hiroyuki Takagi, both of Nagoya, all of Japan

[73] Assignee: Aisin Seiki Kabushiki Kaisha, Nagoya, Japan

[21] Appl. No.: 772,657

[22] Filed: Oct. 7, 1991

[30] Foreign Application Priority Data

Oct. 5, 1990 [JP] Japan .................................. 2-267947

[51] Int. Cl.$^5$ ............................................. A61N 1/362
[52] U.S. Cl. ................................................ 600/16; 623/3
[58] Field of Search ...................................... 600/16–18; 128/24.2, 44, 64; 623/3

[56] References Cited

U.S. PATENT DOCUMENTS

| | | | |
|---|---|---|---|
| 4,794,910 | 1/1989 | Mushika | 600/18 |
| 4,796,606 | 1/1989 | Mushika | 600/18 |
| 4,832,005 | 5/1989 | Takamiya et al. | 600/18 |
| 4,974,774 | 12/1990 | Nakagawa et al. | 600/18 |

Primary Examiner—Lee S. Cohen
Assistant Examiner—John P. Lacyk
Attorney, Agent, or Firm—Sughrue, Mion, Zinn, Macpeak & Macpeak

[57] ABSTRACT

A pump unit for assisting in the blood feeding operation of a heart includes a pair of pumps 7a, 7b connected in parallel with each other. When the pump 7a (or 7b) has reached its expanded position and the pump 7b (or 7a) has reached its contracted position, the operation is changed so that the pump 7a (or 7b) is set up for contraction while the pump 7b (or 7a) is set up for expansion. A time difference TCM between the time when the expanded position is reached and the time when the contracted position is reached is determined. If TCM>Tr, a driving pressure for contraction is changed to a higher value while if TCM<Tr, a driving pressure for contraction is changed to a lower value. Tr represents a non-responsive interval which can be adjusted by an operator. When Tr has a high value, the pump exhibits a low flow rate which serves as a drive to assist in the delivery of blood by the heart. In this manner, the operator is enabled to adjust the driving flow rate.

6 Claims, 6 Drawing Sheets

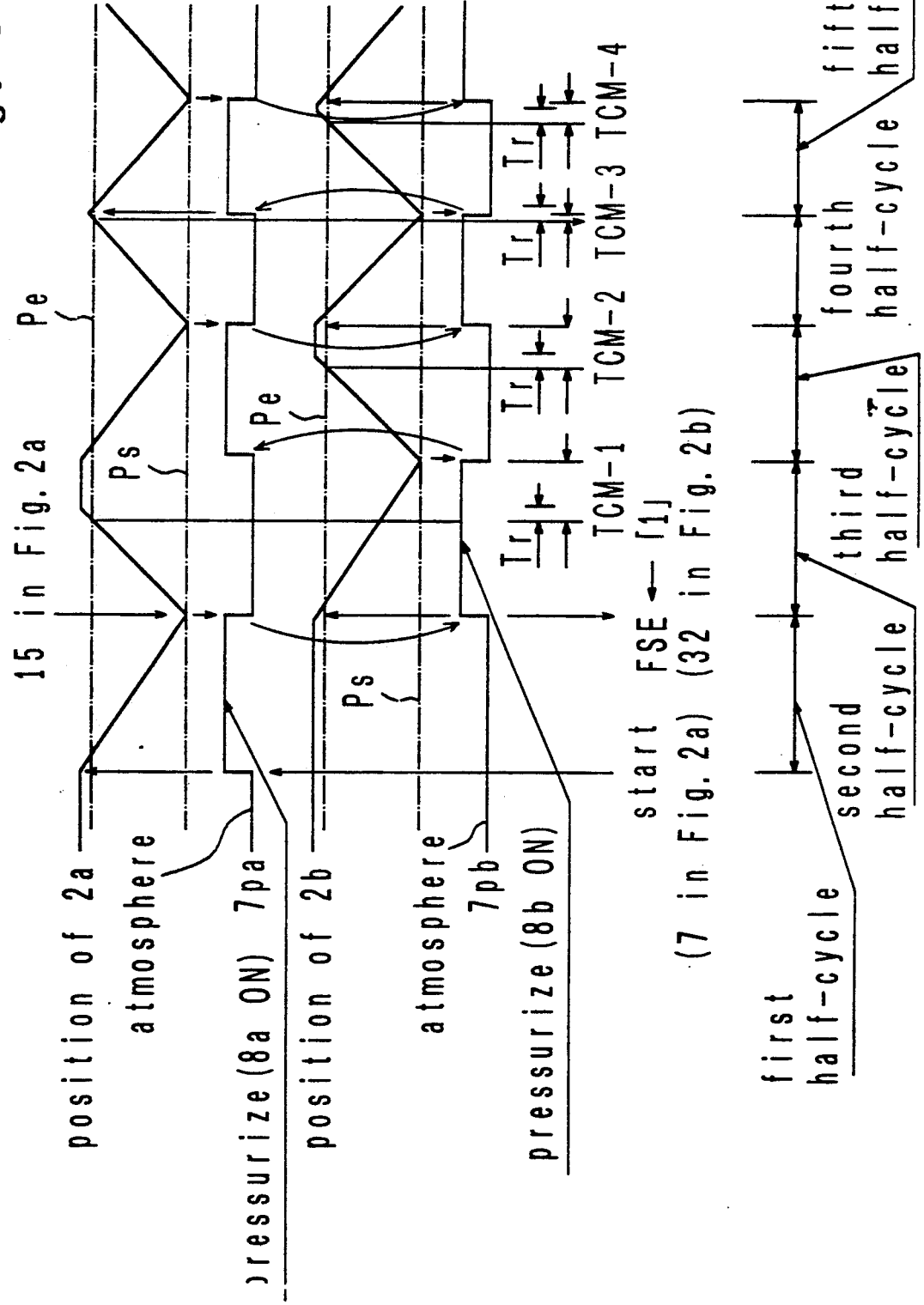

FLUID FEEDING PUMP UNIT

FIELD OF THE INVENTION

The invention relates to a fluid feeding pump unit which delivers a fluid under pressure as it is received at a fluid inlet, and in particular, though not intended to be limited thereto, to a pump unit which is useful in assisting in the functioning of a heart by delivering a blood, as it is fed from the left atrium, under pressure, to the aorta while substantially maintaining the flow rate.

BACKGROUND OF THE INVENTION

An artificial heart is known in the art which delivers the blood to the aorta by withdrawing it from the heart as an example of an assisting in the functioning of a heart. However, it is undesirable to apply a significantly strong external action upon the heart by applying a negative pressure to withdraw the blood which exceeds the capability of the heart to feed the blood. For this reason, it is desirable to provide a pumping action which only assists in the discharge from the heart, in effect, by delivering the blood fed from the heart under pressure while maintaining the flow rate.

Japanese Laid-Open Patent Application No. 94,171/1987 discloses a pump unit including a pair of pumps which are connected in parallel to each other between the left atrium of the heart and the aorta so that during a period when one of the pumps contains a blood discharged from the heart (diastole), the other pump is pressurized to deliver the blood which is contained therein under pressure to the aorta (systole), the both pumps being operated in alternate fashion. Each pump includes an operating pressure chamber to which a drive pressure is applied and a sack disposed within the operating pressure chamber to surround a space into which a blood is received. In order to prevent an excessive negative pressure from being applied to the heart, the operating pressure chamber of the pump is made to communicate with the atmosphere during the diastole so as to allow the blood to enter the blood receiving space within the sack of the pump autonomously under the influence of the discharge pressure of the heart. The sack is responsive to the pressure within the operating pressure chamber to contract, shrinking the blood receiving space whenever the pressure is above the atmosphere, and to expand, increasing the blood receiving space in response to the pressure of the blood which flows into the blood receiving space whenever the operating pressure chamber communicates with the atmosphere. In order to monitor the contracting/expanding motion of the sack, a location on the sack which undergoes a reciprocating movement of a maximum stroke is detected, and the value of a positive pressure applied to the both pumps is controlled in a manner dependent on a time interval counted from the arrival of the given location on the sack of one pump to a given expanded position until a corresponding location on the sack of the other pump reaches a given contracted position, such that such time interval is substantially zero, meaning that the termination of the expansion (suction) of the one pump occurs concurrently with the termination of the contraction (discharge) of the other pump, whereupon the diastole and the systole of the both pumps are changed. In this manner, the pump unit is effective to deliver the blood under pressure to the aorta without causing a disturbance in the flow rate which is discharged from the heart. Since the pumped or delivered flow rate (or drive flow rate) varies automatically tracking a variation in the discharge flow rate from the heart, the pumping action cannot cause any significant loading on the heat. In this manner, an assistance in the functioning of the heart which deliver the blood is realized in a manner which suitably fits the actual operating condition of the heart or the physiological status of a living body, in particular, a change therein.

It will be appreciated that when the living body or the heart recovers, the pump unit must be removed from the living body. However, it is difficult to determine the degree of recovery of the living body or the heart while the pump unit is being used to assist in the blood feeding action of the heart.

Such determination will be greatly facilitated if the operation of the pump unit is stopped. However, if the operation of the pump unit is stopped when the assisting in the blood feeding operation is actually needed, there results a significant risk upon the living body. Accordingly, the need for an assistance by the pump unit must be determined by seeing if the actual flow rate being delivered does not exhibit a substantial decrease or if the actual flow rate being delivered decreases in a manner corresponding to a decrease in the assisting functioning of the pump unit or by seeing a response of the living body while gradually decreasing the blood feeding assisting function (drive flow rate) of the pump unit. Specifically, if the blood is fed under the influence of the discharge pressure from the heart to pass through the pump unit to appear at its outlet to show no change in the actual flow rate being delivered or if a reduction in the flow rate being delivered is small enough to deny an indication of a physiologically bad condition of the living body when the flow rate being delivered by the pump unit (or the drive flow rate) is reduced, a satisfactory recovery of the living body or the heart can be declared. However, it is difficult with the described pump unit to perform such adjustment, namely, reducing the assisting effect upon the blood feeding action in a gentle and smooth manner.

With an ordinary pump, the flow rate being delivered (or the drive flow rate) can be regulated by reducing a drive pressure. However, in the pump unit as described above, when the drive pressure is changed, the drive pressure will be automatically regulated so that the flow rate being delivered substantially matches the flow rate of the in-flow, and accordingly a change in the drive pressure merely results in a temporary disturbance in the pumping action without permitting an adjustment of the contribution of the pump unit in controlling the flow rate being delivered.

SUMMARY OF THE INVENTION

It is an object of the invention to enable an adjustment of a driving flow rate in a pump unit as mentioned above which delivers a fluid under pressure with a flow rate which is substantially equal to the flow rate of an in-flow.

A pump unit according to the invention comprises a first pump (7a) including a first pumping member (5a) which divides the interior of the first pump into a first fluid receiving space (7fa) and a first operating fluid space (7pa) and reciprocable in a direction to cause a contraction/expansion of the first fluid receiving space (7fa), a first check valve (3a) disposed between a fluid inlet (23) and the first fluid receiving space (7fa) for permitting a flow of the fluid from the inlet to the first fluid receiving space while blocking a flow thereof in the opposite direction, and a second check valve (4a) disposed between a fluid outlet (24) and the first fluid receiving space (7fa) for permitting a flow of the fluid from the first fluid receiving space to the outlet while blocking a flow thereof in the opposite direction: first sensor means (1a, 2a) for detecting a contraction and an expansion of the first pumping member (5a);

a second pump (7b) including a second pumping member (5b) dividing the interior of the second pump into a second fluid receiving space (7fb) and a second operating fluid space (7pb) and reciprocable to cause a contraction/expansion of the second fluid receiving space (7fb), a third check valve (3b) disposed between the fluid inlet (23) and the second fluid receiving space (7fb) for permitting a flow of the fluid from the inlet to the second fluid receiving space while blocking a flow thereof in the opposite direction, and a fourth check valve (4b) disposed between the fluid outlet (24) and the second fluid receiving space (7fb) for permitting a flow of the fluid from the second fluid receiving space to the outlet which blocking a flow thereof in the opposite direction: second sensor means (1b, 2b) for detecting a contraction and an expansion of the second pumping member (5b);

a source of high pressure fluid (9, 10, 11p, m);

pressure control means (14c, 18) for controlling the pressure of the source to a given pressure;

first switching means (8a) for selectively connecting the first operating fluid space (7pa) of the first pump (7a) with the source (9, 10, 11p, m) or a low pressure (an atmospheric pressure);

second switching means (8b) for selectively connecting the second operating fluid space (7pb) of the second pump (7b) with the source (9, 10, 11p, m) or a low pressure (an atmospheric pressure);

means (22) for commanding a desired flow rate;

and flow rate control means (18) for commanding a given pressure of the pressure control means (14c, 18), causing the first switching means (8a) to connect the first operating fluid space (7pa) to the source (9, 10, 11p, m) and causing the second switching means (8b) to connect the second operating fluid space (7pb) to the low pressure, the flow rate control means (18) being operable when such connection is established to cause the first switching means (8a) to connect the first operating fluid space (7pa) to the low pressure (atmospheric pressure) whenever the first sensor means (1a, 2a) detects the contraction and then to cause the second switching means (8b) to connect the second operating fluid space (7pb) to the source (9, 10, 11p, m) whenever the aforementioned contraction is detected and the second sensor means (1b, 2b) detects the expansion, the flow rate control means (18) being operable when the described connection is established to cause the second switching means (8b) to connect the second operating fluid space (7pb) to the low pressure whenever the second sensor means (1b, 2b) detects the contraction and to cause the first switching means (8a) to connect the first operating fluid space (7pa) to the source (9, 10, 11p, m) whenever the contraction is detected and the first sensor means (1a, 2a) detects the expansion, and the flow rate control means (18) determining a time difference (TCM) between the time when the contraction is detected and the time when the expansion is detected, the time difference (TCM) assuming a positive value when the expansion is detected earlier and assuming a negative value otherwise, the flow rate control means (18) updating the pressure value (Pt) which is commanded to the pressure control means (14c, 18) in accordance with a value (TCM−Tr, −TCM−Tr) which is obtained by subtracting a value (Tr) which corresponds to a value commanded by the commanding means (22) from the time difference (TCM), thus to a higher or a lower value in accordance with the subtracted value.

It is to be noted that reference numerals and characters appearing in parentheses refer to elements or parts used in an embodiment to be described later with reference to the drawings.

In accordance with the invention, the first and the second pump deliver fluid alternately, one is contracting while the other is expanding. During the systole, the first or the second operating fluid space (7pa or 7pb) assume the low pressure (atmospheric pressure), so that the fluid which is oncoming to the fluid inlet (23) at a pressure level equal to or greater than the low pressure is allowed to flow into the inlet with a rate (flow rate) which corresponds to the pressure level.

The pressure of the source of high pressure fluid (9, 10, 11p, m) is regulated so that the systole of one of the pumps is initiated at a time delay (Tr), corresponding to the pressure value (Tr) commanded by the commanding means (22) to the pressure control means (14c, 18), after the expansion is detected in the other pump (7a or 7b). Thus, the length of the non-responsive time interval is determined by the value (Tr). The greater this value, the lower the rate at which the pump operates and hence the less the flow rate being delivered by the pump (drive flow rate). When the value (Tr) is equal to zero, a steady-state flow rate of blood to be supplied form the left atrium of the heart to the fluid inlet (23) substantially matches the flow rate being delivered by the pump.

As described above, the value (Tr) is commanded by the flow rate commanding means (22). Accordingly, the operator is able to choose an arbitrary value (Tr) by utilizing the means (22). This means that the flow rate being delivered by the pump can be regulated. By way of example, when the operator gradually increases the value (Tr) using the commanding means (22), the flow rate being delivered by the pump (7a or 7b) will decrease in a gradual manner. If the actual flow rate of blood which is delivered to the aorta by the pumps (7a, 7b) do not exhibit a decrease even though the flow rate is gradually decreased, this means that the fluid pressure or the discharge pressure from the heart which reaches the fluid inlet (23) of the pumps (7a, 7b) is sufficiently high that the oncoming fluid pressure itself can be relied on to deliver the fluid to the aorta without recourse to the drive pressure from the pumps (7a, 7b). In this instance, it may be concluded that the assistance by the pump unit is substantially unnecessary, or that the heart is recovering. If the actual flow rate being delivered by the pumps (7a, 7b) decrease with a gradual increase in the value (Tr) which is caused by the flow rate commanding means (22), this means that the delivery of the fluid (blood) is actually dependent on the functionings of the pumps (7a, 7b) or its driving flow rate, so that it may be concluded that the assistance by the pump unit is just required.

Thus it will be seen that the flow rate being delivered by the pump unit can be regulated. In addition, any contribution of the pump unit to the delivery of the fluid can be easily and safely determined without producing any particular oscillation or shock in the delivery of the fluid.

Other objects and features of the invention will become apparent from the following description of an embodiment thereof with reference to the drawings.

BRIEF DESCRIPTION OF THE DRAWINGS

FIG. 1a being a cross section of pumps and connected solenoid operated switching valves and FIG. 1b being a block diagram of a pressure source supplying pressurized air and an electrical unit which controls the pumping operation;

FIG. 3 is a timing chart representing pressures applied to the operating fluid chambers 7pa, 7pb and the positions of the sacks 2a, 2b of the pumps shown in FIG. 1a in a time sequence.

DESCRIPTION OF PREFERRED EMBODIMENT

Figure 1A:
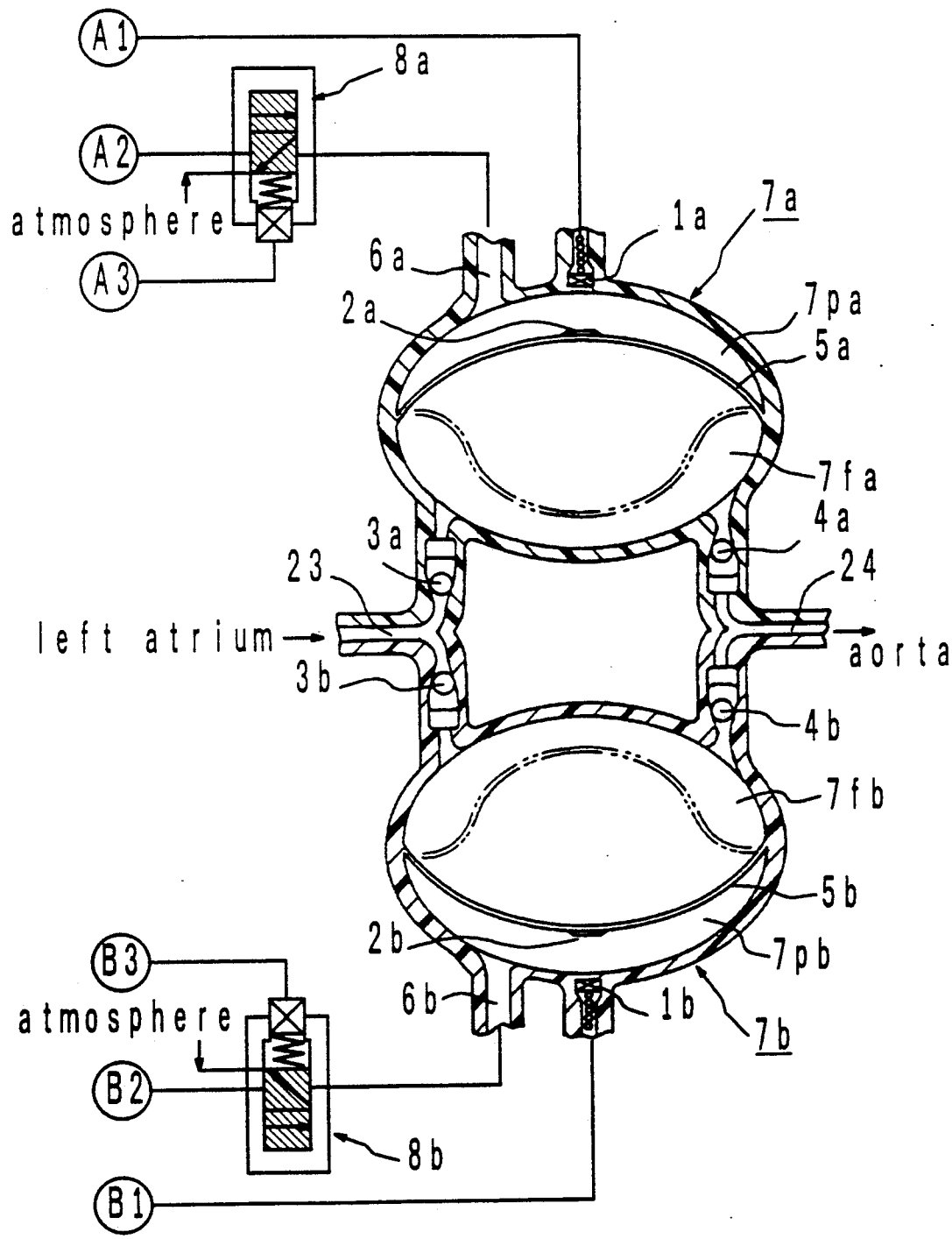
FIGS. 1a and 1b, when combined together, illustrate one embodiment of the invention.
Figure 1B:
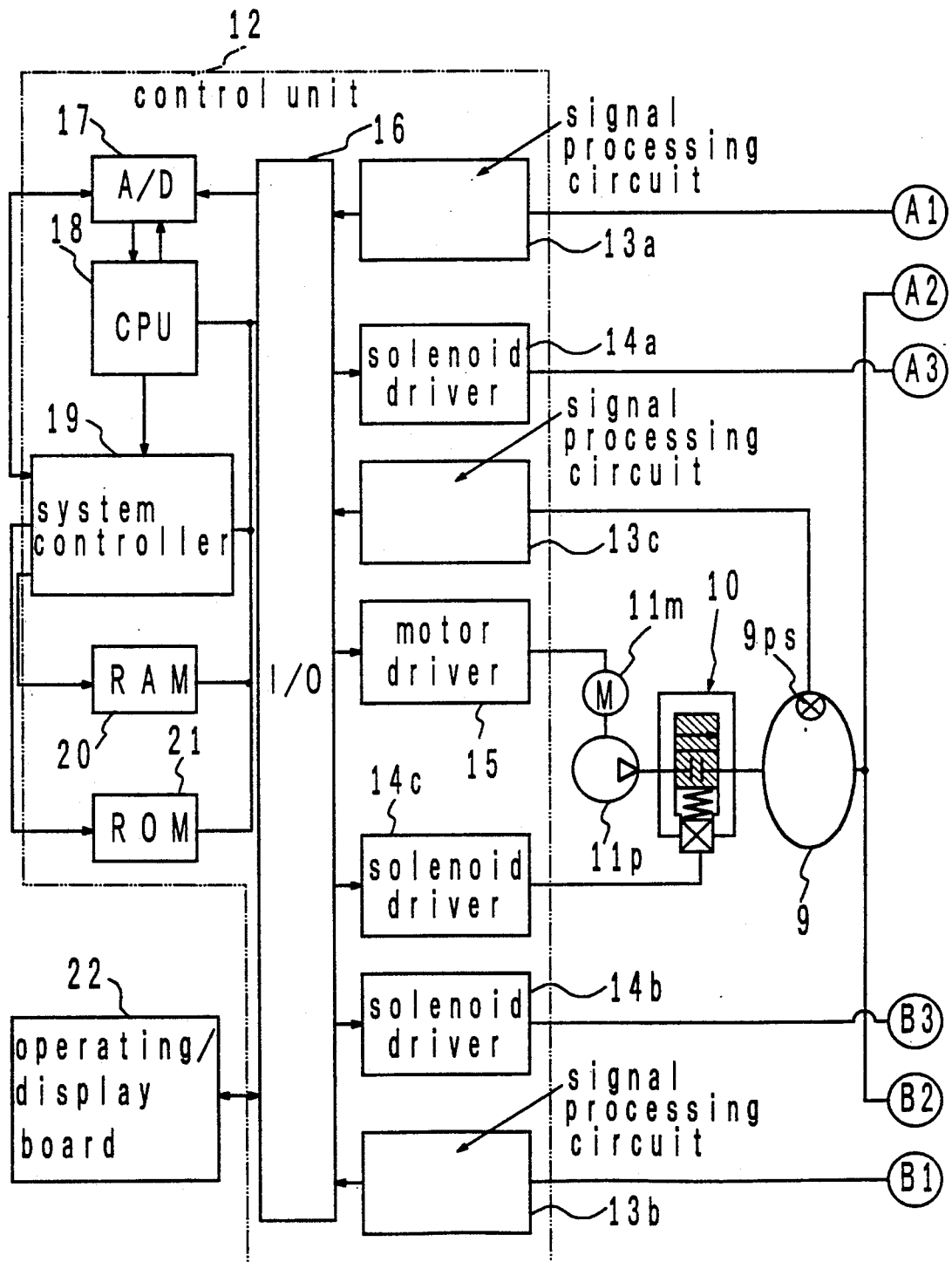

FIGS. 1a and 1b show one embodiment of the invention. FIG. 1a illustrates a pair of pumps 7a, 7b, and a pair of solenoid operated switching valves 8a, 8b which alternately supply an atmospheric pressure (low pressure) and a high pressure air to the pumps. FIG. 1b shows a source for supplying a high pressure air and an associated control unit. It is to be noted that FIGS. 1a and 1b are joined together by combining encircled characters shown in both Figures together to construct the entire arrangement of the embodiment.

In the description to follow, it is assumed that the pumps 7a, 7b are designed to work in combination as an artificial heart, with the fluid inlet 23 being connected to the left atrium of the heart of a living body such as a patient while the fluid outlet 24 is connected to the aorta.

The internal space of the first pump 7a is divided by a sack 5a into a blood or fluid receiving space 7fa and an air or operating fluid receiving space 7pa. The blood which is oncoming to the fluid inlet 23 presses open a ball 3a of the first check valve to enter the blood receiving space 7fa, and then acts, by its own pressure, or under the influence of the air pressure of the air receiving space 7pa which acts upon the sack 5a to contract the blood receiving space 7fa, to press open the ball 4a of a second check valve, thereby passing through the fluid outlet 24 to the aorta.

The air receiving space 7pa is connected to an output port of a first solenoid operated switching valve 8a through an air port 6a. The switch valve 8a has an input port connected to an accumulator 9. Accordingly, when an electrical coil of the switching valve 8a is energized, a valve member of the switching valve is driven to connect the output port (or space 7pa) to the input port (or accumulator 9), but when the coil is deenergized, a coiled compression spring disposed therein returns the valve member, thereby connecting the output port (or space 7pa) to the atmospheric pressure or a port communicating to the atmosphere.

The accumulator 9 is connected to an output port of a solenoid operated open/close valve 10, an input port of which is connected to a discharge port of an air pump 11p, which is driven by an electric motor 11m to deliver a high pressure air. When an electrical coil of the valve 10 is energized, a valve member therein is driven to connect its output port to its input port, whereby the discharge pressure from the air pump 11p is supplied to the accumulator 9. When the coil is deenergized, a coiled compression spring disposed therein returns the valve member to interrupt the communication between the pump 11p and the accumulator 9. During the operation of the pumps 7a, 7b, the air pressure from the accumulator 9 is detected by a pressure sensor 9ps. When the detected pressure is below a target pressure (Pt), the valve 10 is opened, while the valve is closed when the detected pressure is above the target pressure, thus substantially maintaining the target pressure (Pt).

Accordingly, when the first switching valve 8a is electrically energized (on), air of a target pressure (Pt) is supplied to the air receiving space 7pa of the first pump 7a, so that the sack 5a expands to the position, shown in phantom line in FIG. 1a, thus tending to contract the blood receiving space 7fa (contracting step). When the first valve 8a is electrically deenergized (off), the air receiving space 7pa assumes the atmospheric pressure, and the sack 5a moves toward the air port 6a (expanding step) owing to the pressure of the blood which is oncoming to the fluid inlet 23.

A magnetized member 2a in the form of a sheet of ferrite permanent magnet is bonded to the sack 5a at its central position, and a Hall element IC 1a is disposed directly above it. The Hall element 1a is able to detect the strength of a magnetic field produced by the magnetized member 2a, and provides an electrical signal indicative of it, which is applied to a signal processing circuit 13a in a control unit 12.

The second pump 7b has the same construction as the first pump 7a. Parts of the second pump 7b which correspond to parts of the first pump 7a are designated by like reference characters in which "a" is replaced by "b".

The second pump 7b is driven for a contraction/expansion by turning a second solenoid-operated switching valve 8b on and off. The second pump 7b is also provided with a Hall element IC 1b, producing a detected signal which is applied to a signal processing circuit 13b within the control circuit 12.

The signal processing circuits 13a and 13b are effective to convert an electrical signal representing the strength of a magnetic field to an analog distance signal. At this end, the Hall elements 1a and 1b produce analog signals representing the distance or spacing of the sacks 5a and 5b as referenced to the Hall elements 1a and 1b, which signals are applied to an A/D converter 17 through input/output (I/O) unit 16. It is to be noted that the distance or the location of the sacks 5a, 5b are referenced to the Hall elements 1a and 1b. Accordingly, when the sacks 5a, 5b are located near their contracted position, the analog signal exhibits high level while the signal level will be low when the sacks are located near their expanded position.

The electrical coils of the first and the second switching valves 8a and 8b are connected to the solenoid drivers 14a and 14b, respectively, which are contained in the control unit 12. Responsive to a command from a microprocessor (hereafter referred to as CPU), the drivers 14a and 14b turn the electrical coils on and off. The electrical coil of the solenoid-operated open/close valve 10 is connected to a solenoid driver 14c, which in turn turns this electrical coil on and off in response to a command from CPU 18.

The electric motor 11m which drives the air pump 11p is connected to a motor driver 15, which in turn turns the motor 11m on and off in response to a command from CPU 18.

The pressure sensor 9ps produces an electrical signal which represents the internal pressure within the accumulator 9, and applies this signal to a signal processing circuit 13c. The circuit 13c converts this signal into an analog signal having a level which maintains a linear relationship with the input signal, and the analog signal is fed to the A/D converter 17 through the input/output unit 16.

CPU 18 within the control unit 12 is connected to a system controller 19, RAM 20 and ROM 21. The control unit 12 is connected to an operating/display board 22 which includes a power switch, data input keys, a two-dimensional display, indicator lights and a buzzer.

Figure 2A:
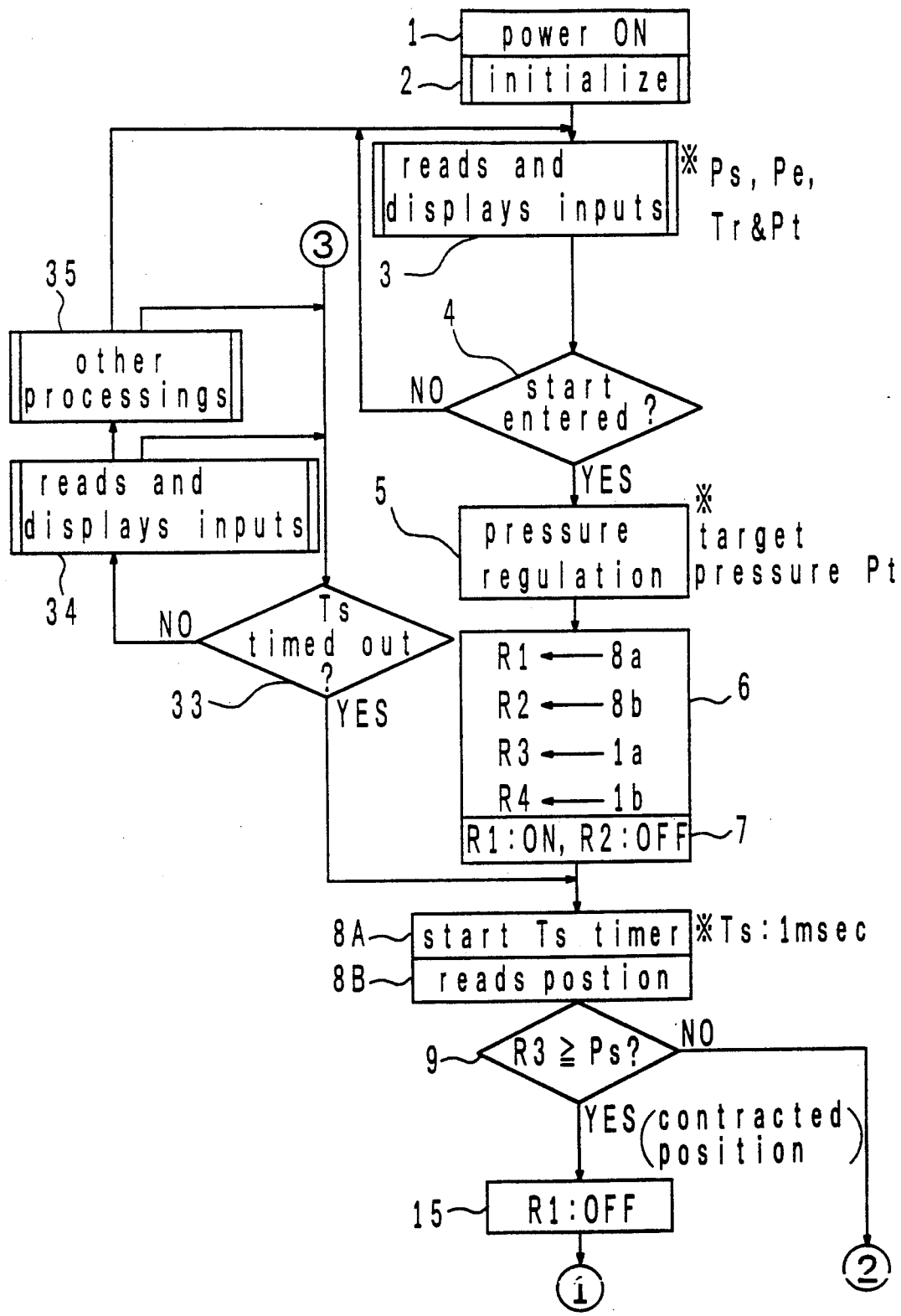
FIGS. 2a, 2b and 2c are flow charts indicating a control operation of CPU 18 shown in FIG. 1b.
Figure 2B:
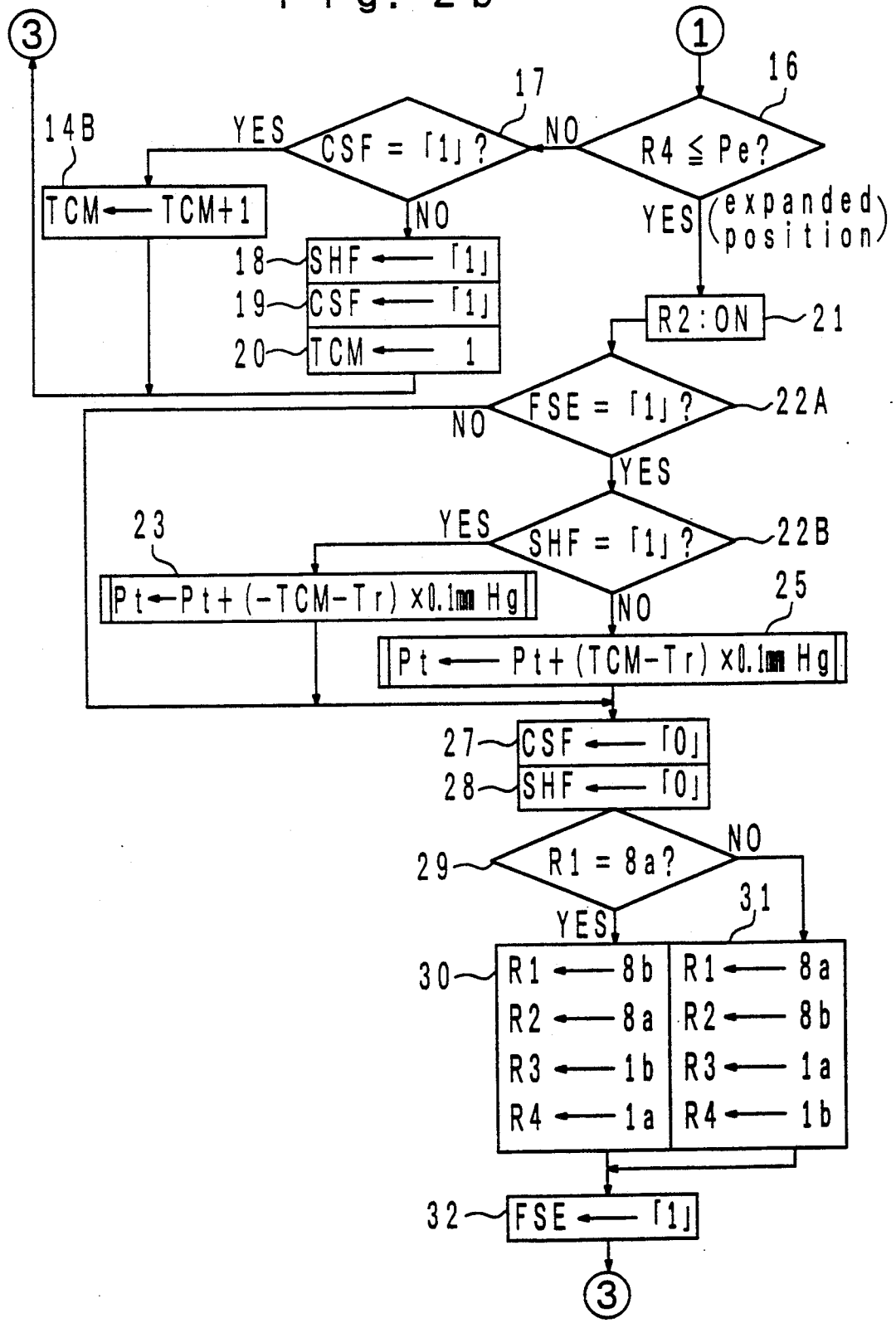
Figure 2C:
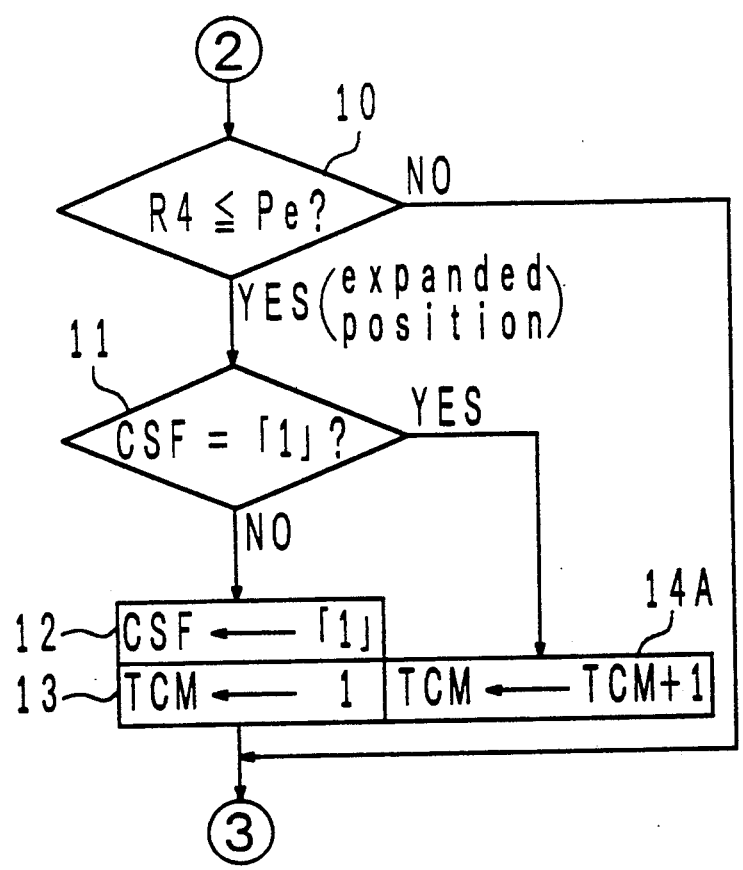

FIGS. 2a, 2b and 2c illustrate a control operation by CPU 18, and FIG. 3 shows changes occurring in the pressures of the blood receiving spaces 7pa, 7pb of the pumps 7a, 7b and changes in the position of the sacks 5a, 5b which occur as a result of the control operation.

Referring to FIG. 2a, a power supply to the unit is turned on, and given voltages are applied to various parts of the unit (step 1). CPU 18 then clears internal registers, counters, timers or the like, and delivers default signals (i.e., signals turning solenoid-operated valves off and turning motors off) to all its output ports. It then writes a standard value Ps into contracted position registers Psa (associated with pump 7a) and Psb (associated with pump 7b), writes a standard value Pe into expanded position registers Pea (associated with pump 7a) and Peb (associated with pump 7b), clears a non-responsive interval register Tr, and writes a standard pressure Pts into a target pressure register Pt (step 2). It then displays entry items, associated numerical figures which are chosen to set-up the pump unit, and a guidance sentence urging an operator to make an entry (step 3). The entry items and numerical figures set up are as follows:

Contracted position
  first pump "Psa: Ps"
  second pump "Psb: Ps"
Expanded position
  first pump "Pea: Pe"
  second pump "Peb: Pe"
Non-responsive interval-"Tr: 0"
Target pressure-"Pt: Pts"

where Ps, Pe, 0, Pts are numeral figures and the guidance sentence is as indicated below:

"* If any modification is desired, move a cursor to a location to be modified and make an entry of a desired numerical figure.

* Press a start key to initiate the operation and press a stop key to stop the operation."

When any modification entry is made, CPU 18 reads it, and then changes the display to a corresponding one while simultaneously updating the content of registers accordingly (step 3). It then waits for the start key to be depressed (steps 3, 4, 3).

When the start key is depressed, CPU 18 energizes the motor 11m to drive the air pump 11p, and then turns the solenoid-operated switching valve 10 on, thus opening it. It then reads the pressure detected by the pressure sensor 9ps through the A/D converter 17, and waits for the detected pressure to become equal to or exceeds the content Pt of the target pressure register Pt. When the detected pressure from the pressure sensor 9ps reaches or exceeds Pt, it initiates a constant pressure control routine, not shown, (wherein the detected pressure from the pressure sensor 9ps is read periodically, turning the open/close valve 10 off if the detected pressure is equal to or above Pt, and turning the valve 10 on if the detected pressure is below Pt) (step 5).

(1) Control over a first half-cycle

CPU 18 sets up the first pump 7a for contraction and the second pump 7b for expansion (step 6), and turns the valve 8a connected to the pump 7a which is set up for contraction on and turns the valve 8b connected to the pump 7b which is set up for expansion off (step 7). Ts timer is started (step 8A). In this embodiment, Ts is equal to 1 msec.

Referring to FIGS. 2a, 2b and 2c, CPU 18 re-starts Ts timer at step 8A, reads position detecting signals from the Hall elements 1a and 1b (the distances of the sacks 5a, 5b as referenced to the Hall elements) (step 8B), examines if the sack 5a of the pump 7a which is set up for contraction has reached its contracted position (step 9) or examines if the sack 5b of the pump 7b which is set up for expansion has reached its expanded position (step 10) with a period of 1 msec or each time the Ts timer times out. If the answer to either examination is found to be in the affirmative, it increments a count register TCM by one (steps 9, 15 to 20 or steps 9 to 13) and subsequently increments it by one every time 1 msec Ts passes (steps 14B or 14A). If the contracted position is reached, CPU 18 turns the solenoid-operated open/close valve 8a connected to the pump 7a which is set up for contraction off (step 15).

If the contracted position is reached before the expanded position is reached, "1" is entered into a flag register SHF to indicate this (steps 9, 15, 16, 17, 18). If either the contracted position or the expanded position is reached, "1" is entered into a flag register CSF to indicate this (step 19 or 12).

(2) Control over a second half-cycle

If both the contracted position and the expanded position are reached, CPU 18 reads the count TCM from the count register TCM, and turns the solenoid-operated open/close valve 8b connected to the pump 7b on (step 21), thus setting up the pump 7a for expansion and the pump 7b for contraction (steps 21, 22A, 27, 28, 29, 30).

When so switched, CPU 18 refers to the count TCM (in unit of msec) and the content of flag registers FSE and SHF, and does not modify the target pressure Pt, to be described later, since the content of FSE is equal to "0" (thus inhibiting a modification of the target pressure Pt: During the first half-cycle, the pump 7b is set up for expansion, and the sack 5b assumes its expanded position before the unit starts to operate and thus undergoes no displacement, whereby the count TCM represents an error). When switching from the first to the second half-cycle (steps 29, 30), the content of the flag register FSE is changed to "1", thus enabling the target pressure Pt to be modified (step 32).

CPU 18 then repeats re-starting Ps timer (step 8A), reading position detecting signals from the Hall elements 1a and 1b (step 8B), examination to see if the sack 5a of the pump 7b which is set up for contraction has reached its contracted position (step 9) or if the sack 5a of the pump 7a which is set up for expansion has reached its expanded position (step 10). When either the contracted or expanded position is reached, it begins incrementing the count register TCM (steps 9, 15 to 20, 14B or steps 9 to 13, 14A). When the contracted position is reached, CPU 18 turns the solenoid-operated open/close valve 8b connected to the pump 7b which is set up for contraction off (step 15).

When the contracted position is reached before the expanded position is reached, "1" is entered into the flag register SHF to indicate this (steps 9, 15, 16, 17, 18). Either the contracted or the expanded position is reached, "1" is entered into the flag register CSF to indicate this (step 19 or 12).

(3) Control over a third half-cycle

When both the contracted and expanded position are reached, CPU 18 then reads the count TCM from the count register TCM, and turns the solenoid-operated open/close valve 8a connected to the pump 7a on (step 21), thus setting up the pump 7b for expansion and the pump 7a for contraction (steps 21, 22A, 22B, 23, 25, 27, 28, 29, 31).

Modification of target pressure Pt

During this switching operation, CPU 18 refers to the count TCM (in unit of msec) and the content of the flag registers FAC and SHF, and since the content of FAC is equal to "1" (enabling a modification of the target pressure Pt) it then examines the content of the flag register SHF, and if the content is equal to "1", meaning that the pump which is set up for contraction has reached its contracted position before the pump which is set up for expansion has reached its expanded position, thus indicating the need to reduce target pressure Pt, it calculates $$Pt+(-TCM-Tr)\times 0.1$$

where the content of the target pressure register Pt is represented by Pt in unit of mmHg and Tr represents the content of the non-responsive interval register Tr. The value thus calculated is entered into the target pressure register Pt to update it (step 23).

When the content of the flag register SHF is equal to "0", meaning that the pump which is set up for expansion has reached its expanded position before the pump which is set up for contraction has reached its contracted position, CPU 18 calculates $$Pt+(TCM-Tr)\times 0.1$$

and enters this calculated value into the target pressure register Pt to update it (step 25).

CPU 18 executes a constant pressure control routine, not shown, in which the solenoid-operated open/close valve 10 is turned on or off so that the detected pressure from the pressure sensor 9ps corresponds to a pressure indicated by a data from the target pressure register Pt. When the content of the target pressure register Pt is changed during the updating operation (steps 23, 25) mentioned above, the pressure of the accumulator, or the positive driving pressure which is supplied to the pumps 7a and 7b from the open/close valves 8a and 8b is changed.

Upon switching from the second and the third half-cycle (steps 29, 30), CPU 18 modifies the content of the flag register FSE to "1", thus enabling a modification of the target pressure Pt (step 32).

CPU 18 then repeats re-starting the Ts timer (step 8A), reading of position detecting signals from the Hall elements 1a and 1b (step 8B), and the examination to see if the sack 5a of the pump 7a which is set up for contraction has reached its contracted position (step 9) or if the sack 5b of the pump 7b which is set up for expansion has reached its expanded position (step 10). When either the contracted or the expanded position is reached, it begins incrementing the count register TCM (steps 9, 15 to 20, 14B or steps 9 to 13, 14A). When the contracted position is reached, CPU 18 turns the solenoid-operated open/close valve 8a connected to the pump 7a which is set up for contraction off (step 15).

When the contracted position is reached before the expanded position is reached, "1" is entered into flag register SHF to indicate this (steps 9, 15, 16, 17, 18). When either the contracted position or the expanded position is completely reached, "1" is entered into flag register CSF to indicate this (step 19 or 12).

(4) Control over a fourth half-cycle

When both the contracted and the expanded position are reached, CPU 18 then reads the count TCM from the count register TCM, and turns the solenoid-operated open/close valve 8b connected to the pump 7b on (step 21), thus setting up the pump 7a for expansion and the pump 7b for contraction (steps 21, 22A, 22B, 23, 25, 27, 28, 29, 30). During this switching operation, the "modification of target pressure Pt" mentioned above is executed similarly. In other respects, the operation is similar to the "control over second half-cycle" mentioned above.

(5) Control over a fifth and subsequent half-cycle

Control over a fifth and a subsequent odd-numbered half-cycle remain the same as the "control over third half-cycle" mentioned above, and a control over a sixth and a subsequent even-numbered half-cycle remain the same as the "control over fourth half-cycle" mentioned above.

By repeating the described operation, the pump driving pressure Pt changes automatically so that at a time delay Tr after the pump which is set up for expansion has reached its expanded position, the pump which is set up for contraction reaches its contracted position, whereupon the former pump is switched for contraction while the latter pump is switched for expansion. A process of such pressure regulation is illustrated in FIG. 3.

It is to be noted at step 33, Ts timer is examined if it has timed out. If it is found that the Ts timer has timed out, it is re-started (step 8A), and the position of the sack is read (step 8B). During the time the microprocessor waits for the timer to time out, any entry to the operating/display board 22 is monitored (step 34). Any entry is processed accordingly (step 35). In the absence of any entry, the microprocessor goes on monitoring the time-out of the timer (step 33). If there occurs an entry specifying Tr, for example, during the time the micro-processor is monitoring the time-out, such entry is read and is used to update the register Tr, subsequently returning to the monitoring of the timer's time-out (step 33). Accordingly, the operator is allowed to modify Tr even during the time the pumps are being driven. In the event the stop key is depressed during the monitoring of the timer, a stop operation is executed, whereupon the operation returns to step 3.

In the process illustrated in FIG. 3, the time TCM−1 from the termination of the expansion to the initiation of the contraction during the second half-cycle is longer than Tr, and hence the target pressure Pt is updated to a higher value.

As a consequence, during the third half-cycle, the rate at which the contraction occurs (or the driving pressure for contraction) is higher, so that the time TCM−2 from the termination of the expansion to the initiation of the contraction during the third half-cycle is slightly shorter. However, it is still longer than Tr, and so the target pressure Pt is updated to an even higher value.

As a consequence, the rate of contraction during the fourth half-cycle is higher, and the time TCM−3 from the termination of the expansion to the initiation of the contraction during the fourth half-cycle is reduced excessively, and becomes less than Tr, whereby TCM−Tr which is determined during the step 25 assumes a negative value, thus requiring updating the target pressure Pt to a lower value.

As a consequence of this, TCM−4 from the termination of the contraction to the initiation of the expansion during the fifth half-cycle becomes longer and is very close to Tr, whereby a modification to the target pressure Pt is minimal.

In this manner, TCM converges to Tr. Accordingly, when the operator utilizes the operating/display board 22 to modify Tr, the target pressure Pt is automatically changed in accordance therewith so as to bring TCM into coincidence with Tr.

By way of example, when the flow rate at which the heart delivers the blood becomes higher, the expansion period will be reduced, whereby the length of the time TCM increases. The target pressure Pt is then increased, increasing the driving pressure supplied to the pump to reduce the contraction period. conversely, when the flow rate at which the heart delivers the blood is reduced, the expansion period will be longer, whereby the length of the time TCM will be reduced. Stated differently, taking the arrival at the expanded position as a reference, the contracted position will be reached earlier than the expanded position is reached, whereby TCM substantially assumes a negative value. The target pressure Pt is then reduced, reducing the driving pressure supplied to the pump to increase the contraction period. For either variation, the driving pressure supplied to the pumps 7a, 7b is changed in positively corresponding manner to the amount of inflow to the fluid inlet 23 so that the contracted position is reached with a given time delay of Tr after the expanded position is reached, thus changing the flow rate being delivered through the fluid outlet 24. In this manner, the driving output supplied to the pumps 7a, 7b is automatically changed in accordance with a change in the amount of supply from the heart.

It will be understood from the above description of the operation that Tr represents a pause period from the termination of the expansion of one of the pumps to the initiation of the next contraction. The pause period increases by choosing a higher value for Tr, and hence the flow rate being delivered by the pump operation is reduced. If the discharge pressure from the heart is relatively high, the discharge pressure from the heart allows the blood to be fed through the pumps 7a, 7b to the aorta even though the flow rate being delivered by the pumps becomes reduced, and accordingly, the actual flow rate being delivered through the outlet 24 will not exhibit any significant reduction. However, when the discharge pressure from the heart is low, an increase in the length of Tr in the manner mentioned above results in a reduction in the actual flow rate being delivered through the outlet 24. Accordingly, when determining the degree of recovery of the heart, the operator may utilize the operating/display board 22 to update the value of Tr in increments during the pump operation to see the degree to which the actual flow rate of blood being delivered through the pumps 7a, 7b becomes reduced for each increment, thus determining the degree of recovery of the heart.

While an artificial heart has been chosen to describe the embodiment, it should be understood that the pump unit of the invention is not limited in its use to the artificial heart, but is equally applicable to any other application which requires delivering a flow rate under pressure, at a rate equivalent to the flow rate delivered from a supplying source without causing any significant disturbance thereto and which also requires a regulation in the assistance or driving flow rate by the pump unit.

As mentioned, the pump unit according to the invention allows a flow rate of fluid to be delivered under pressure which is equivalent to a flow rate of fluid being delivered by a supplying source in accordance with a change in the flow rate from the source without causing any significant disturbance to the source. The flow rate delivered by the pump unit can be regulated by the flow rate commanding means (22), and a contribution of the pump unit in delivering the fluid can be easily and safely determined without causing any significant oscillation or shock to the source which delivers the fluid.

While an embodiment of the invention has been disclosed above, it should be understood that the invention is not limited thereto, but that a number of changes, modifications and substitutions therein will readily occur to one skilled in the art without departing from the scope and spirit of the invention defined by the appended claims.

What is claimed is:

1. Fluid feeding pump unit comprising
a first pump including a first pumping member which divides the interior of the first pump into a first fluid receiving space having a fluid inlet and a fluid outlet and a first operating fluid space and reciprocable in a direction to contact/expand the first fluid receiving space, a first check valve disposed between the fluid inlet and the first fluid receiving space to permit a flow of the fluid from the former to the latter while blocking a flow thereof in the opposite direction, and a second check valve disposed between the fluid outlet and the first fluid receiving space to permit a flow of fluid from the latter to the former while blocking a flow thereof in the opposite direction;
first sensor means for detecting a contraction and an expansion of the first pumping member;
a second pump including a second pumping member which divides the internal space of the second pump into a second fluid receiving space having a fluid inlet and a fluid outlet and a second operating fluid space and reciprocable to contract/expand the second fluid receiving space, a third check valve disposed between the fluid inlet and the second fluid receiving space to permit a flow of fluid from the former to the latter while blocking a flow thereof in the opposite direction, and a fourth check valve disposed between the fluid outlet and the second fluid receiving space to permit a flow of fluid from the latter to the former while blocking a flow thereof in the opposite direction;
second sensor means for detecting a contraction and an expansion of the second pumping member;
a high pressure fluid source;
a low pressure fluid source;
pressure control means for controlling the pressure of the high pressure fluid source to a specified pressure;

first switching means for selectively connecting the first operating fluid space of the first pump to the high pressure fluid source or the low pressure fluid source;

second switching means for selectively connecting the second operating fluid space of the second pump to the high pressure fluid source or the low pressure fluid source;

flow rate commanding means for commanding a flow rate delivered by the pump unit;

and flow rate control means for commanding a given pressure to the pressure control means to cause the first switching means to connect the first operating fluid space to the high pressure fluid source and to cause the second switching means to connect the second operating fluid space to the low pressure fluid source, the flow rate control means being operable when such connection is established to cause the first switching means to connect the first operating fluid space to the low pressure fluid source whenever the first sensor means has detected the contraction and to cause the second switching means to connect the second operating fluid space to the high pressure fluid source when the first sensor means has detected the contraction and the second sensor means has detected the expansion, the flow rate control means being operable when such connection is established to cause the second switching means to connect the second operating fluid space to the low pressure fluid source whenever the second sensor means has detected the contraction and to cause the first switching means to connect the first operating fluid space to the high pressure fluid source when the second sensor means has detected the contraction and the first sensor means has detected the expansion, and the flow rate control means determining a time difference between the time when the contraction is detected and the time when the expansion is detected, the time difference assuming a positive value when the expansion is detected earlier than the contraction is detected and assuming a negative value otherwise, the flow rate control means updating a commanded pressure to the pressure control means in accordance with the time difference from which a value corresponding to a commanded value from the flow rate commanding means is subtracted, thus to a higher commanded pressure when the subtracted value is higher, or to a lower commanded pressure when the subtracted value is lower.

2. Fluid feeding pump unit according to claim 1 in which the first switching means comprises a first solenoid-operated switching valve including an output port communicating with the first operating fluid space of the first pump, a high pressure port communicating with the high pressure fluid source, a low pressure port open to the atmosphere, a valve member for selectively connecting the output port to the high pressure port or the low pressure port, and an electrical coil for driving the valve member to a position in which the output port is connected to the high pressure port when it is electrically energized, and wherein the second switching means comprises a solenoid-operated second switching valve including an output port communicating with the second operating fluid space of the second port, a high pressure port communicating with the high pressure fluid source, a low pressure port open to the atmosphere, a valve member for selectively connecting the output port to the high pressure port or the low pressure port, and an electrical coil for driving the valve member to a position in which the output port is connected to the high pressure port when it is electrically energized.

3. Fluid feeding pump unit according to claim 2 in which the source of high pressure fluid comprises an air accumulator including an input port, an output port communicating to the output ports of the first and the second solenoid-operated valves, a pressure accumulating space communicating with the ports, and a pressure sensor for detecting the pressure in the presure accumulating space;

a solenoid-operated open/close valve including an input port, an output port communicating to the input port of the air accumulator, a valve member for opening/closing the communication between the input and the output port of the solenoid operated open/close valve, and an electrical coil for driving the valve member to a position in which the input and the output port of the solenoid operated open/close valve communicate with each other when it is electrically energized;

an air pump having a discharge port connected to the input port of the solenoid-operated open/close valve;

and an electric motor for driving the air pump.

4. Fluid feeding pump unit comprising a first pump including a first pumping member which divides the interior of the first pump into a first fluid receiving space having a fluid inlet and a fluid outlet and a first operating fluid space and reciprocable in a direction to contract expand the first fluid receiving space, a first check valve disposed between a fluid inlet and the first fluid receiving space to permit a flow of the fluid from the former to the latter while blocking a flow thereof in the opposite direction, a second check valve disposed between the fluid outlet and the first fluid receiving space to permit a flow of fluid from the latter to the former while blocking a flow thereof in the opposite direction, and first position detecting means for detecting the position of the first pumping member;

a second pump including a second pumping member which divides the internal space of the second pump into a second fluid receiving space having a fluid inlet and a fluid outlet and a second operating fluid space and reciprocable to contract/expand the second fluid receiving space, a third check valve disposed between the fluid inlet and the second fluid receiving space to permit a flow of fluid from the former to the latter while blocking a flow thereof in the opposite direction, a fourth check valve disposed between the fluid outlet and the second fluid receiving space to permit a flow of fluid from the latter to the former while blocking a flow thereof in the opposite direction, a second position detecting means for detecting the position of the second pumping member;

a high pressure fluid source;

a low pressure fluid source;

pressure control means for controlling the pressure of the high pressure fluid source to a specified pressure;

first switching means for selectively connecting the first operating fluid space of the first pump to the high pressure fluid source or the low pressure fluid source;

second switching means for selectively connecting the second operating fluid space of the second pump to the high pressure fluid source or the low pressure fluid source;

flow rate commanding means for commanding a flow rate delivered by the pump unit;

and flow rate control means for commanding a given pressure to the pressure control means to cause the first switching means to connect the first operating fluid space to the high pressure fluid source and to cause the second switching means to connect the second operating fluid space to the low pressure fluid source, the flow rate control means being operable when such connection is established to cause the first switching means to connect the first operating fluid space to the low pressure fluid source whenever the position detected by the first position detecting means has reached a contracted position and to cause the second switching means to connect the second operating fluid space to the high pressure fluid source when the second sensor means has detected the contraction and the position detected by the second position detecting means has reached an expanded position, the flow rate control means being operable when such connection is established to cause the second switching means to connect the second operating fluid space to the low pressure fluid source whenever the position detected by the second position detecting means has reached its contracted position and to cause the first switching means to connect the first operating fluid space to the high pressure fluid source when the second sensor means has detected the contraction and the position detected by the first position detecting means has reached the expanded position, and the flow rate control means determining a time difference between the time when the contracted position is reached and the time when the expanded position is reached, the time difference assuming a positive value when the expanded position is reached earlier than the contraction is detected and assuming a negative value otherwise, the flow rate control means updating a commanded pressure to the pressure control means in accordance with the time difference from which a value corresponding to a commanded value from the flow rate commanding means is subtracted, thus to a higher commanded pressure when the subtracted value is higher, or to a lower commanded pressure when the subtracted value is lower.

5. Fluid feeding pump unit according to claim 4 in which the first switching means comprises a first solenoid-operated switching valve including an output port communicating with the first operating fluid space of the first pump, a high pressure port communicating with the high pressure fluid source, a low pressure port open to the atmosphere, a valve member for selectively connecting the output port to the high pressure port or the low pressure port, and an electrical coil for driving the valve member to a position in which the output port is connected to the high pressure port when it is electrically energized, and wherein the second switching means comprises a solenoid-operated second switching valve including an output port communicating with the second operating fluid space of the second port, a high pressure port communicating with the high pressure fluid source, a low pressure port open to the atmosphere, a valve member for selectively connecting the output port to the high pressure port or the low pressure port, and an electrical coil for driving the valve member to a position in which the output port is connected to the high pressure port when it is electrically energized.

6. Fluid feeding pump unit according to claim 5 in which the source of high pressure fluid comprises an air accumulator including an input port, an output port communicating to the output ports of the first and the second solenoid-operated valves, a pressure accumulating space communicating with the ports, and a pressure sensor for detecting the pressure in the pressure accumulating space;

a solenoid-operated open/close valve including an input port, an output port communicating to the input port of the air accumulator, a valve member for opening/closing the communication between the input and the output port of the solenoid operated open/close valve, and an electrical coil for driving the valve member to a position in which the input and the output port of the solenoid operated open/close valve communicate with each other when it is electrically energized;

an air pump having a discharge port connected to the input port of the solenoid-operated open/close valve;

and an electric motor for driving the air pump.

* * * * *